United States Patent [19]

Jaeggi

[11] Patent Number: 4,709,092
[45] Date of Patent: Nov. 24, 1987

[54] PROCESS FOR THE PREPARATION OF 2-ALKOXYBENZOSULFONAMIDES

[75] Inventor: Franz-Josef Jaeggi, Baton Rouge, La.

[73] Assignee: Ciba-Geigy Corporation, Ardsley, N.Y.

[21] Appl. No.: 836,288

[22] Filed: Mar. 5, 1986

[51] Int. Cl.$^4$ .......................................... C07C 143/78
[52] U.S. Cl. .................................................. 564/89
[58] Field of Search ........................................ 564/89

[56] References Cited

U.S. PATENT DOCUMENTS 4,476,321 10/1984 Meyer et al. ........................ 564/89
4,510,325  4/1985 Meyer et al. ........................ 564/89
4,556,733 12/1985 Sullivan et al. ..................... 558/89

FOREIGN PATENT DOCUMENTS 0023422 7/1980 European Pat. Off. .
0044807 7/1981 European Pat. Off. .
0044808 7/1981 European Pat. Off. .

Primary Examiner—Anton H. Sutto
Attorney, Agent, or Firm—Edward McC. Roberts; Kevin T. Mansfield

[57] ABSTRACT

In accordance with a novel process, 2-alkoxybenzosulfonamides of formula I

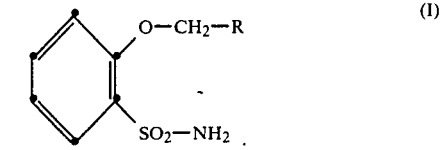

wherein R is chloromethyl, methoxymethyl, $C_1$–$C_4$alkyl or trifluoromethyl, are prepared by reacting a 4-alkoxychlorobenzene of formula II

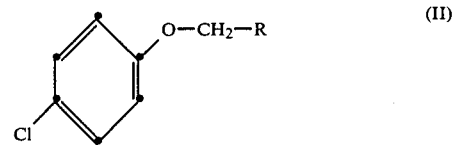

with chlorosulfonic acid $ClSO_3H$, converting the resultant sulfonyl chloride of formula III

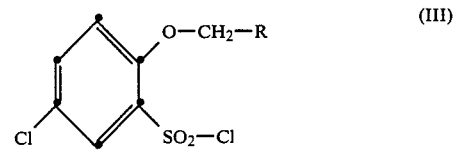

by reaction with ammonia into the sulfonamide of formula IV

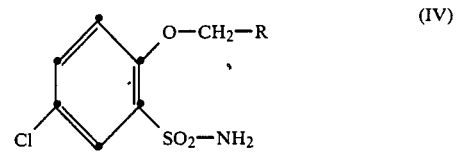

and hydrogenating said sulfonamide with hydrogen, in the presence of a precious metal catalyst.

6 Claims, No Drawings

PROCESS FOR THE PREPARATION OF 2-ALKOXYBENZOSULFONAMIDES

The present invention relates to a novel process for the preparation of 2-alkoxybenzosulfonamides.

The 2-alkoxybenzosulfonamides which can be prepared by the novel process are valuable intermediates for the synthesis of herbicidal 2-alkoxybenzosulfonylureas. This class of highly effective herbicides has recently been described in a large number of patent applications and publications. The 2-alkoxybenzosulfonamides which can be prepared by the process of this invention, the preparation thereof and the use thereof in the synthesis of the herbicidal final products from the class of sulfonylureas are described in European patent application Nos. 23 422, 44 807 and 44 808.

The process hitherto described for the preparation of alkoxybenzosulfonamides are less suitable for large-scale industrial application since either unstable diazonium salts are obtained as intermediates and the exchange reaction of the Sandmeyer type with Cu(I) compounds has only an insufficient degree of selectivity or product mixtures are formed which require complicated separation methods.

There is therefore a need for an inexpensive process for the preparation of 2-alkoxybenzosulfonamides, which process can be carried out on a large industrial scale.

Surprisingly, the novel process of this invention substantially meets these requirements.

In accordance with the present invention, it is proposed to prepare the 2-alkoxybenzosulfonamides of formula I

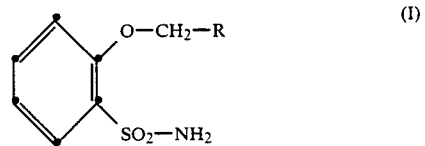

wherein R is chloromethyl, methoxymethyl, $C_1$-$C_4$alkyl or trifluoromethyl, by reacting a 4-alkoxychlorobenene of formula II

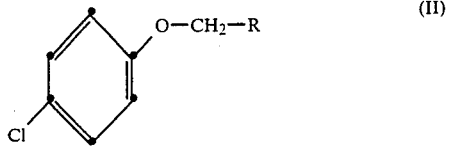

wherein R is as defined for formula I, with chlorosulfonic acid $ClSO_3H$, converting the resultant sulfonyl chloride of formula III

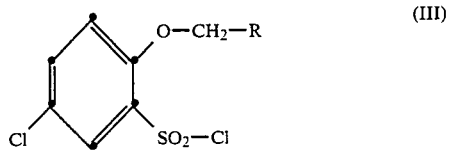

wherein R is as defined for formula I, by reaction with ammonia into the sulfonamide of formula IV

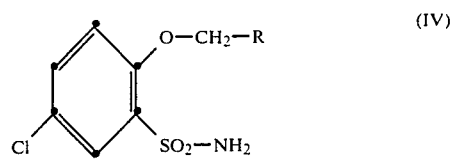

wherein R is as defined for formula I, and hydrogenating said sulfonamide with hydrogen, in the presence of a precious metal catalyst.

In the above definitions, alkyl is methyl, ethyl, n-propyl, isopropyl, n-butyl, sec-butyl, isobutyl, or tert-butyl.

The reaction product of formula I can be converted direct into an agriculturally useful active ingredient of the class of sulfonylureas in a manner known per se by reaction with a suitable pyrimidinylcarbamate or triazinylcarbamate or with a corresponding isocyanate. As an alternative to this process, the 2-alkoxybenzosulfonamides of formula I are first converted into the corresponding isocyanates or carbamates which are then reacted with suitable pyrimidinylamines or triazinylamines to give effective sulfonylureas.

The starting materials of formula II are known and can be obtained by simple etherification reactions from 4-chlorophenol.

Commercially available chlorosulfonic acid is used for carrying out the first step (II→III) of the process of this invention. To effect reaction, at least 3 moles of chlorosulfonic acid are used per mole of the compound of formula II. It is advantageous to employ a larger excess of chlorosulfonic acid, e.g. at least 5 moles of chlorosulfonic acid per mole of the compound of formula II. In individual embodiments, the chlorosulfonic acid may be used as reactant and solvent simultaneously. In general, however, the reaction (II→III) is carried out in an inert solvent. Suitable solvents are carbon disulfide, ethyl acetate, toluene, xylene, saturated hydrocarbons such as hexane, decane or cyclohexane, and chlorinated hydrocarbons such as methylene chloride, chloroform, carbon tetrachloride, 1,2-dichloroethane, 1,2-dichloroethylene, tetrachloroethylene, chlorobenzene or dichlorobenzene. The preferred solvents are cyclohexane, n-decane, methylene chloride, 1,2-dichloroethane and chloroform. The reaction temperatures are usually in the range of from $-10°$ C. to $+100°$ C., preferably from $-10°$ C. to $+80°$ C.

In a preferred embodiment of the first reaction step (II→III), the compounds of formula III are prepared by reacting the corresponding compound of formula II, in an inert solvent and at a temperature in the range from $-10°$ C. to $+100°$ C., with at least 3 times the equimolar amount of chlorosulfonic acid. A particularly preferred embodiment comprises carrying out the reaction (II→III) at a temperature in the range of from $-10°$ C. to $+80°$ C., in methylene chloride, 1,2-dichloroethane or chloroform, with at least 5 times the eqimolar amount of chlorosulfonic acid.

The first reaction step (II→III) may also be carried out using an equimolar amount of chlorosulfonic acid, in which case an additional reaction step is necessary. The economic and ecological advantages reside in the fact that by using an equimolar amount of chlorosulfonic acid, there is no excess of chlorosulfonic acid to be worked up or neutralised. In accordance with this process variant, the compounds of formula II are reacted, at a temperature in the range from $0°$ C. to $+150°$ C., preferably from +20° C. to +60° C., with an equimolar amount of chlorosulfonic acid or with a slight excess thereof. In this case, working up does not directly yield the sulfonyl chloride of formula III, but neutralisation of the reaction mixture with aqueous alkali metal hydroxide, at a temperature in the range from 0° C. to +100° C., preferably from +50° C. to +90° C., yields the corresponding sulfonic acid alkali metal salt of fomula V

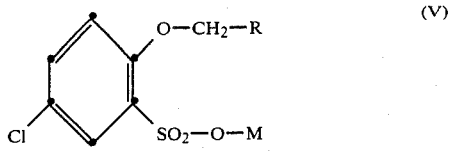

(V)

wherein R is as defined for formula I and M is a sodium or potassium atom. This reaction is advantageously carried out in an inert solvent such as an alkane or chloroalkane. In favourable cases, e.g. if all reaction components are liquid at the selected reaction temperature, a solvent can be dispensed with and the reaction can be carried out with the pure reactants. Solvents of the above-mentioned type are pentane, hexane, heptane, octane, decane, dodecane, and also cyclopentane or cyclohexane, as well as methylene chloride, chloroform, carbon tetrachloride, dichloroethane, trichlorethane or tetrachloroethane. Cyclohexane and n-decane are preferred.

The compound of formula V is converted into the sulfonyl chloride of formula III by reaction with customary chlorinating agents such as phosphoroxy chloride, thionyl chloride or, preferably, phosgene. It is advantageous to use a catalyst such as dimethylformamide or dimethylacetamide. The reaction conditions for the genesis of the sulfonyl chloride from the free acid or alkali metal salt (V→III) correspond to the usual conditions for this type of reaction. The exclusion of moisture and neutrality of the solvent are essential features. Such conditions are indicated above in the description of the direct preparation of the sulfonyl chloride (II→III). Preferred reaction temperatures are in the range from +60° C. to +120° C.

The conversion of the sulfonyl chloride of formula III into the corresponding sulfonamide of formula IV is effected under the conditions usual for this per se known reaction step, for example by adding an aqueous solution of ammonia to the compound of formula III, under normal pressure and at a temperature in the range from 0° C. to +100° C., preferably from 0° C. to +30° C.; or by treating a compound of formula III with ammonia, in an inert solvent, optionally in the presence of an acid acceptor. Examples of solvents and acid acceptors are: carbonates such as sodium carbonate and potassium carbonate, bicarbonates such as sodium bicarbonate and potassium bicarbonate, oxides such as calcium oxide and magnesium oxide, or hydroxides such as sodium hydroxide, potassium hydroxide, calcium hydroxide or magnesium hydroxide; ethers such as diethyl ether, tetrahydrofuran, dioxane, ethylene glycol dimethyl ether or diethylene glycol dimethyl ether; ketones such as acetone, 2-butanone, 3-pentanone or cyclohexanone; chlorinated hydrocarbons such as chlorobenzene, dichlorobenzene, methylene chloride, chloroform, carbon tetrachloride, trichloroethane or getrachloroethane; secondary alcohols such as 2-butanol, isopropanol or cyclohexanol; or hydrocarbons such as cyclohexane, benene, toluene or xylene. The reaction is preferably carried out with an aqueous solution of ammonia in the pesence of toluene or xylene. The dechlorination of the compound of formula IV to give the compound of formula I by catalytic hydrogenation with hydrogen is generally carried out under mild conditions, in the temperature range from +20° C. to +70° C., in the pressure range from 1 to 5 bar, preferably from 1 to 1.5 bar, in an inert solvent and in the presence of an acid acceptor. In general, the catalysts employed are precious metal catalysts such as platinum in the form of platinum oxide or palladium, platinum black or platinum on barium sulfate, palladium black or palladium on carbon. The catalyst which can be most widely used is palladium on carbon in commercially available form as 5% palladium on carbon. Acid acceptors normally employed are: hydroxides such as sodium hydroxide or potassium hydroxide, metal salts of carboxylic acids, e.g. sodium acetate, salts of phosphoric acid, e.g. disodium phosphate, bicarbonates, oxides such as magnesium oxide or calcium oxide, as well as, preferably, tertiary organic amines such as trimethylamine, triethylamine, diazabicyclo[2.2.2]octane, 1,8-diazabicyclo[5.4.0]undec-7-ene, 1,5-diazabicyclo[4.3.0]non-5-ene, pyridine, quinoline or isoquinoline. Suitable solvents are: ethers such as diethyl ether, tetrahydrofuran or dioxane: ketones such as acetone, 2-butanone or cyclohexanone; esters such as ethyly acetate; alcohols such as methanol, ethanol, n-propanol, isopropanol or butanol; and hydrocarbons such as pentane, hexane, cyclohexane, benzene, toluene or xylene; or water. In the preferred embodiment, the compound of formula IV is hydrogenated with hydrogen, under normal pressure, in the temperature range from +50° C. to +55° C. and in the presence of a 5% palladium on carbon catalyst in a mixture of 2-butanone and water.

A preferred embodiment of the process of this invention for the preparation of compounds of formula I comprises reacting a compound of formula II, at a temperature in the range from +20° C. to +60° C. and in n-decane, with an equimolar amount of chlorosulfonic acid; neutralising the reaction mixture with alkali metal hydroxide, at a temperature in the range from +50° C. to +90° C.; adding phosgene to the resultant sulfonic acid alkali metal salt of formula V, in xylene and at a temperature in the range from +60° C. to +120° C.; treating the resultant sulfonyl chloride of formula III with an aqueous solution of ammonia, in the presence of toluene or xylene; and dechlorinating the resultant sulfonamide of formula IV by catalytic hydrogenation with hydrogen, in a 2-butanone/water/base mixture, under normal pressure, at a temperature in the range from +20° C. to +70° C. and in the presence of a 5% palladium on carbon catalyst.

The intermediates of formulae III, IV and V are novel. They have been specially developed for carrying out the process of this invention and therefore constitute an object of the present invention.

The invention is illustrated in more detail by the following Examples. Example P2 shall be understood as being an alternative to the first and second reaction steps of Example P1.

PREPARATORY EXAMPLES

Example P1: 2-(2-Chloroethoxy)benzosulfonamide (a) 2-(2-Chloroethoxy)-5-chlorobenzosulfonic acid sodium salt With vigorous stirring, 122 g (1.05 moles) of chlorosulfonic acid are added over 2 hours, at a temperature in the range from +35° C. to +40° C., to a solution of 191 g (1.00 mole) of 4-chloro-(2-chloroethoxy)benzene in 300 ml of n-decane. Hydrogen chloride gas evolves and a precipitate forms. The reaction solution is heated to +80° C., 50 ml of water are added and the mixture is neutralised to pH 7 by the addition of 160 g of a 30% (1.20 moles) solution of sodium hydroxide. The hot aqueous phase is separated and 700 ml of xylene are added to it. The water is expelled from this mixture by distillation with a water separator, whereupon the salt-like product precipitates from the xylene solution and a suspension forms. Optional filtration and drying affords 302 g (100% of theory) of 2-(2-chloroethoxy)-5-chlorobenzosulfonic acid sodium salt.

The corresponding potassium salt and the sodium or potassium salts of 2-(2-methoxyethoxy)-5-chlorobenzosulfonic acid and 2-(2,2,2-trifluoroethoxy)-5-chlorobenzosulfonic acid are obtained in analogous manner.

(b) 2-(2-Chloroethoxy)-5-chlorobenzosulfonyl chloride 1.5 g (0.02 mole) of dimethylformamide are added, at a temperature in the range from +85° C. to +90° C., to the suspension [obtained in step (a)] of 302 g of 2-(2-chloroethoxy)-5-chlorobenzosulfonic acid sodium salt in 700 ml of xylene. 150 g (1.51 moles) of gaseous phosgene are subsequently introduced into the mixture over 2 hours. Excess phosgene is expelled by introducing nitrogen gas for 30 minutes. 200 ml of water are added at 50° C. to the mixture. The organic phase is separated and concentrated by evaporation, affording 287 g (99.2% of theory) of 2-(2-chloroethoxy)-5-chlorobenzosulfonyl chloride with a melting point of 94.5°–95° C.

2-(2-Methoxyethoxy)-5-chlorobenzosulfonyl chloride (as an oil) and 2-(2,2,2-trifluoroethoxy)-5-chlorobenzosulfonyl chloride (m.p.: 76° C.) are obtained in analogous manner.

(c) 2-(2-Chloroethoxy)-5-chlorobenzosulfonamide 142 g of a 30% (2.5 moles) solution of ammonia are added over 2 hours, at a temperature in the range from +55° C. to +60° C., to the solution [obtained in step (b)] of 287 g of 2-(2-chloroethoxy)-5-chlorobenzosulfonyl chloride in 700 ml of xylene. A colourless crystalline precipitate forms. The temperature is held for a further 2 hours at +55° C. and subsequently lowered to 0° C. The crystalline precipitate is separated and washed three times with isopropanol (with one 150 ml portion and with two 500 ml portions). The product is dried, affording 250 g (92.6% of theory) of 2-(2-chloroethoxy)-5-chlorobenzosulfonamide with a melting point of 145° C.

2-(Methoxyethoxy)-5-chlorobenzosulfonamide (m.p.: 121°–123° C.) and 2-(2,2,2-trifluoroethoxy)-5-chlorobenzosulfonamide (m.p.: 142.5° C.) are obtained in analogous manner.

(d) In an agitator flask, a mixture consisting of 67.5 g (0.25 mole) of 2-(2-chloroethoxy)-5-chlorobenzosulfonamide, 165 g of 2-butanone, 36 g of water, 3.4 g of 5% palladium on carbon and 0.22 g of acetic acid is hydrogenated with hydrogen, at a temperature in the range from +50° C. to +55° C. under normal pressure. During the hydrogenation reaction, the pH is held constant at pH 6 to 6.5 by the dropwise addition of 33.5 g of a 30% (0.25 mole) solution of sodium hydroxide. The reaction time required until the mixture is saturated with hydrogen is 45 minutes. The product is obtained by filtering the mixture and concentrating the filtrate. The yield is 58.2 g (99% of theory) of 2-(2-chloroethoxy)benzosulfonamide with a melting point of 119° C.

2-(2-Methoxyethoxy)benzosulfonamide (m.p.: 111° C.) and 2-(2,2,2-trifluoroethoxy)benzosulfonamide (m.p.: 123° C.) are obtained in analogous manner.

Example P2:
2-(2-Chloroethoxy)-5-chlorobenzosulfonyl chloride

With stirring, 64.0 g (0.33 mole) of 4-chloro-(2-chloroethoxy)benzene are added dropwise over 0.5 hours, at a temperature of +5° C., to a solution of 233 g (2 moles) of chlorosulfonic acid in 105 ml of 1,2-dichloroethane. The reaction mixture is stirred for a further 1½ hours at 20° C. and then taken up in a mixture consisting of 230 g of ice, 170 ml of water and 60 ml of 1,2-dichloroethane. The organic phase is separated, washed with water and concentrated by evaporation, affording 77 g (80% of theory) of 2-(2-chloroethoxy)-5-chlorobenzosulfonyl chloride.

2-n-Propoxy-5-chlorobenzosulfonyl chloride, 2-ethoxy-5-chlorobenzosulfonyl chloride, 2-(2-methoxyethoxy)-5-chlorobenzosulfonyl chloride and 2-(2,2,2-trifluoroethoxy)-5-chlorobenzosulfonyl chloride are obtained in analogous manner.

What is claimed is:

1. A process for the preparation of a 2-alkoxybenzosulfonamide of formula I

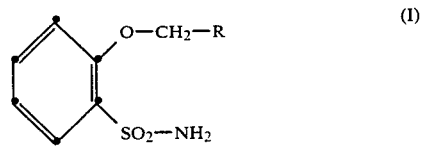

wherein R is chloromethyl, methoxymethyl, $C_1$–$C_4$alkyl or trifluoromethyl, which process comprises reacting a 4-alkoxychlorobenzene of formula II

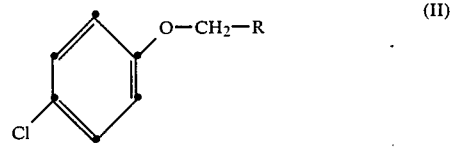

wherein R is as defined for formula I, at a temperature between 0° C. and +150° C. with about one equivalent of chlorosulfonic acid, neutralizing the reaction mixture with an aqueous solution of alkali metal hydroxide at a temperature between 0° C. and +100° C. and converting the resultant sulfonic acid alkali metal salt of formula V

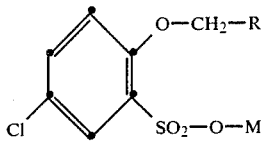

wherein R is as defined for formula I and M is a sodium or potassium atom, by reaction with a chlorinating agent at a temperature between +60° C. and +120° C. into the sulfonyl chloride of formula III

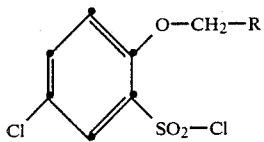

wherein R is as defined for formula I, and converting said sulfonyl chloride with ammonia into the sulfonamide of formula IV

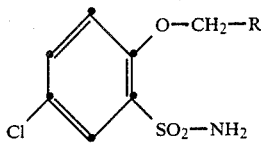

wherein R is as defined for formula I, and hydrogenating said sulfonamide with hydrogen at a temperature between +20° C. and +70° C. and at a pressure range from 1 to 5 bar in an inert solvent and in the presence of a precious metal catalyst and an acid acceptor.

2. A process according to claim 1, wherein the individual reaction steps are carried out in inert solvents.

3. A process according to claim 1, wherein the neutralization to give the compound of formula IV is carried out in an aqueous solution of ammonia and in the presence of toluene or xylene.

4. A process according to claim 1, wherein the dechlorination of the compound of formula IV to give the compound of formula I is carried out with hydrogen, in the pressure range from 1 to 5 bar, at a temperature in the range from +20° C. to +70° C. and in the presence of a 5% palladium on carbon catalyst in a mixture of 2-butanone and water.

5. A process according to claim 1, wherein the compound of formula III is reacted, at a temperature in the range from +20° C. to +60° C., with 1 equivalent of chlorosulfonic acid in cyclohexane or n-decane; the solution is neutralised with aqueous alkali metal hydroxide, at a temperature in the range from +50° C. to +90° C.; and the sulfonic acid alkali metal salt of formula V is converted, at a temperature in the range from +60° C. to +120° C., by reaction with phosgene into the sulfonyl chloride of formula III.

6. A process according to claim 1, wherein a comound of formula II is reacted, at a temperature in the range from +20° C. to +60° C. and in n-decane, with 1 equimolar amount of chlorosulfonic acid; the reaction mixture is neutralised with alkali metal hydroxide, at a temperature in the range from +50° C. to +90° C.; phosgene is added to the resultant sulfonic acid alkali metal salt of formula V, in xylene and at a temperature in the range from +60° C. to +120° C.; the resultant sulfonyl chloride of formula III is treated with an aqueous solution of ammonia, in the presence of toluene or xylene; and the resultant sulfonamide of formula IV is dechlorinated by catalytic hydrogenation with hydrogen, in a mixture of 2-butanone and water, under normal pressure, at a temperature in the range from +20° C. to +70° C. and in the presence of a 5% palladium on carbon catalyst.

* * * * *